United States Patent
Perez

(10) Patent No.: US 10,391,066 B2
(45) Date of Patent: Aug. 27, 2019

(54) COMPOSITIONS AND METHODS FOR THE TREATMENT OF PARKINSON'S DISEASE

(71) Applicant: Ruth Perez, El Paso, TX (US)

(72) Inventor: Ruth Perez, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 14/435,346

(22) PCT Filed: Oct. 18, 2013

(86) PCT No.: PCT/US2013/065694
§ 371 (c)(1),
(2) Date: Apr. 13, 2015

(87) PCT Pub. No.: WO2014/063057
PCT Pub. Date: Apr. 24, 2014

(65) Prior Publication Data
US 2015/0290145 A1    Oct. 15, 2015

Related U.S. Application Data

(60) Provisional application No. 61/716,313, filed on Oct. 19, 2012.

(51) Int. Cl.
*A61P 25/16*     (2006.01)
*A61K 31/137*    (2006.01)
*A61K 31/66*     (2006.01)
*A61K 45/06*     (2006.01)
*A61K 31/165*    (2006.01)

(52) U.S. Cl.
CPC .......... *A61K 31/137* (2013.01); *A61K 31/165* (2013.01); *A61K 31/66* (2013.01); *A61K 45/06* (2013.01)

(58) Field of Classification Search
None
See application file for complete search history.

(56) References Cited

U.S. PATENT DOCUMENTS 8,309,768 B2 * 11/2012 Chen ............... C07C 217/64
                                                 564/336
2005/0090520 A1 * 4/2005 Lindquist ......... A61K 9/0043
                                                 514/291
2008/0221200 A1    11/2008 Allison et al.

FOREIGN PATENT DOCUMENTS

EP        0627406 B1 * 10/1998 ......... C07C 215/10
WO        2005025553 A2     3/2005
WO        WO2010/097371  *  9/2010 ......... A61K 31/165

OTHER PUBLICATIONS

De Sarno et al., Lithium Prevents and Ameliorates Experimental Autoimmune Encephalomyelitis. J Immunol 2008; 181:338-345.*
Schiffmann et al., Inhibitors of specific ceramide synthases. Biochimie 94 (2012) 558-565 (Year: 2012).*

(Continued)

*Primary Examiner* — Aurora M Fontainhas
(74) *Attorney, Agent, or Firm* — Chainey P. Singleton

(57) ABSTRACT

The present invention provides a method for treating, alleviating, reversing or delaying progression of at least one symptom of Parkinson's Disease in a subject in need thereof by administering to the subject an effective amount of a 2-amino-2[2-(4-octylphenyl)ethyl]propane-1,3-diol composition or a derivative thereof to treat at least one symptom of Parkinson's Disease.

13 Claims, 10 Drawing Sheets

(56) References Cited

OTHER PUBLICATIONS

Smith et al., Mitochondria-Targeted Antioxidants in the Treatment of Disease. Mitochondria and Oxidative Stress in Neurodegenerative Disorders: Ann. N.Y. Acad. Sci. 1147: 105-111 (2008). (Year: 2008).*

International Report on Patentability [RU] PCT/US2013/065694 dated Apr. 30, 2015.

Trufanov, AA et al. "Modern Ideas of Levodopa Preparations, Their Efficacy and Tolerability in Patients With Parkinson's Disease", International Journal of Neurology 7 (45) 2011.

* cited by examiner

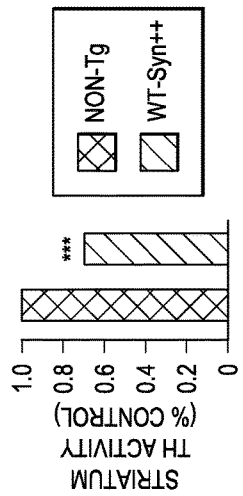
FIG. 2A
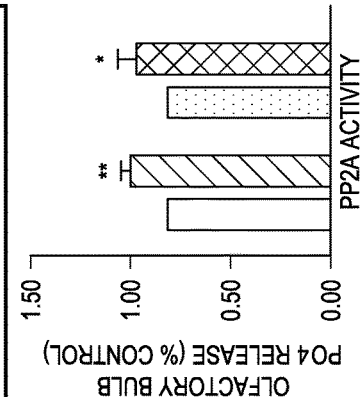
FIG. 2B
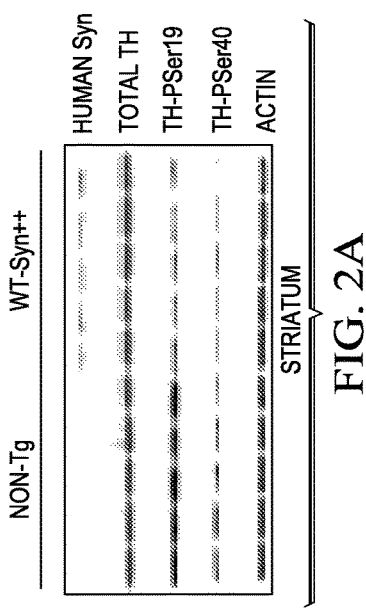
FIG. 2D
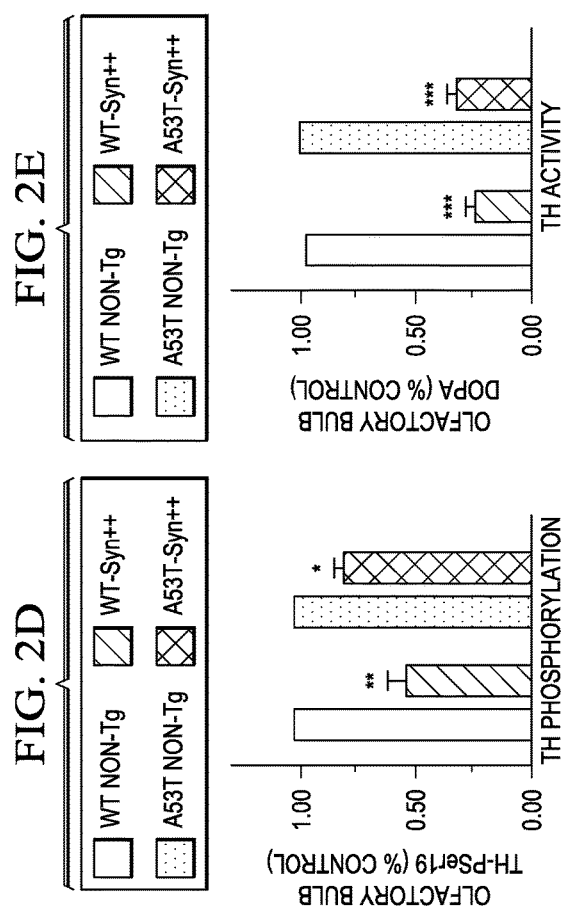
FIG. 2E
FIG. 2F

COMPOSITIONS AND METHODS FOR THE TREATMENT OF PARKINSON'S DISEASE

CROSS-REFERENCE TO RELATED APPLICATIONS

This application claims priority to, and is the National Stage of International Application No. PCT/US2013/065694 filed on Oct. 18, 2013 and claims the priority of U.S. Provisional Patent Application Ser. No. 61/716,313, filed on Oct. 19, 2012, the contents of which are incorporated by reference herein in their entirety.

TECHNICAL FIELD OF THE INVENTION

The present invention relates generally to the field of neurodegeneration and inflammatory diseases of the central and peripheral nervous system. More particularly, it concerns methods for treating Parkinson's Disease using 2-amino-2-[2-(4-octylphenyl)ethyl]-1,3-propanediol.

BACKGROUND ART

Without limiting the scope of the invention, its background is described in connection with the composition and treatment of inflammatory diseases of the nervous system. For example, U.S. Pat. No. 8,258,150, entitled, "Treatment of Inflammatory Diseases," discloses a method for treating inflammatory diseases of the peripheral nervous system by modulating Sphingosine-1-phosphate receptor activity and provides a method of treating a subject with chronic inflammatory demyelinating polyneuropathy or other autoimmune neuropathies comprising administering to the subject an effective amount of FTY720.

U.S. Pat. No. 7,811,822, entitled, "Modulation of Neural Stem Cells and Neural Progenitor Cells," discloses methods of influencing central nervous system cells to produce progeny useful in the treatment of CNS disorders by exposing a patient suffering from such a disorder to a reagent that modulates the proliferation, migration, differentiation and survival of central nervous system cells via S1P or LPA signaling.

U.S. Patent Application Publication No. 2005/0090520, entitled "Treatment of Disease or Injury of the Nervous System with FTY720," discloses methods for modulating neurogenesis in vitro and in vivo by contacting neural stem cells with an effective amount of a FTY720 compound. The neurogenesis may involve the modulation of proliferation, differentiation, migration or survival of a non-embryonic neural stem cells or progenitor cells. Also disclosed are methods for the prevention or treatment of neurological disorders by administering to a subject a therapeutically effective amount of FTY720 compound.

U.S. Patent Application Publication No. 2006/0046979, entitled "Organic Compounds," discloses pharmaceutical combinations comprising at least one S1P receptor agonist, as well as a method for treating demyelinating diseases, e.g., multiple sclerosis or disorders associated therewith or Guillain-Barre syndrome (GBS), comprising co-administration, e.g., concomitantly or in sequence, of a therapeutically effective amount of an Shingosine 1-Phosphate (S1P) receptor agonist, and at least one co-agent shown to have clinical activity against at least one symptom of a demyelinating disease.

DISCLOSURE OF THE INVENTION

The present disclosure provides an effective amount of a FTY720 composition for use in the treatment of at least one symptom of Parkinson's Disease. The FTY720 composition is in the form of a free form FTY720 or a pharmaceutically acceptable FTY720 salt. The FTY720 composition is administered orally. The FTY720 composition is co-administered with at least one active agent shown to have clinical activity against at least one motor symptom of Parkinson's Disease. The FTY720 composition is administered to the subject prior to the onset of at least one motor symptom of Parkinson's Disease. The FTY720 composition is 2-amino-2-[2-(4-octylphenyl)ethyl]-1,3-propanediol. The FTY720 composition is 2-amino-2-[2-(4-octylphenyl)ethyl]propane-1,3-diol phosphate, (N-(1-hydroxy-2-(hydroxymethyl)-4-(4-octylphenyl)butan-2-yl)ethanamide), ((3-(1-hydroxy-2-(hydroxymethyl)-4-(4-octylphenyl)butan-2-ylamino)-3-oxopropyl)triphenylphosphonium bromide) or a derivative thereof.

The present disclosure provides an effective amount of a FTY720 composition for use in alleviating or delaying progression of at least one symptom of Parkinson's Disease. The composition further includes at least one active agent comprises an effective amount of an immunosuppressant, a corticosteroid, an immunoglobulin or a combination thereof. The FTY720 composition is 2-amino-2-[2-(4-octylphenyl)ethyl]-1,3-propanediol. The FTY720 composition is 2-amino-2-[2-(4-octylphenyl)ethyl]propane-1,3-diol phosphate, (N-(1-hydroxy-2-(hydroxymethyl)-4-(4-octylphenyl)butan-2-yl)ethanamide), ((3-(1-hydroxy-2-(hydroxymethyl)-4-(4-octylphenyl)butan-2-ylamino)-3-oxopropyl)triphenylphosphonium bromide) or a derivative thereof.

The present disclosure provides a composition for treating, alleviating or delaying progression of the symptoms of Parkinson's Disease comprising: a pharmaceutical carrier containing a 2-amino-2-[2-(4-octylphenyl)ethyl]propane-1,3-diol composition or a derivative thereof in an effective amount to ameliorate at least one symptom of Parkinson's Disease. The pharmaceutical carrier is formulated for oral delivery. The composition further comprising at least one additional active agent shown to have clinical activity against at least one symptom of a demyelinating disease. At least one active agent comprises an effective amount of an immunosuppressant, a corticosteroid, an immunoglobulin or a combination thereof.

The present disclosure provides an effective amount of a FTY720 composition for use in the treatment or prevention of at least one motor symptom of Parkinson's Disease in a subject suspected of having Parkinson's Disease wherein the FTY720 composition is selected from

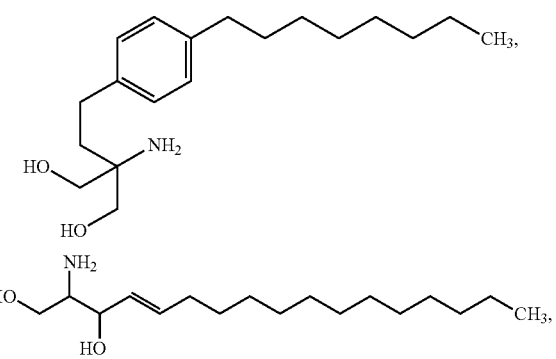

-continued

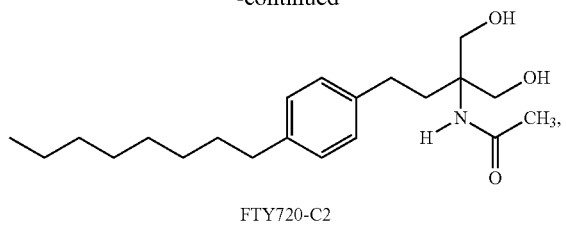

FTY720-C2

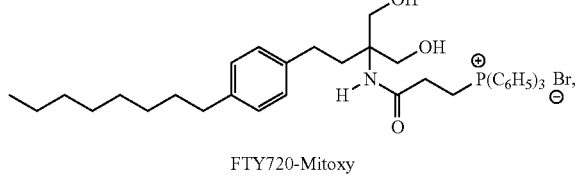

FTY720-Mitoxy

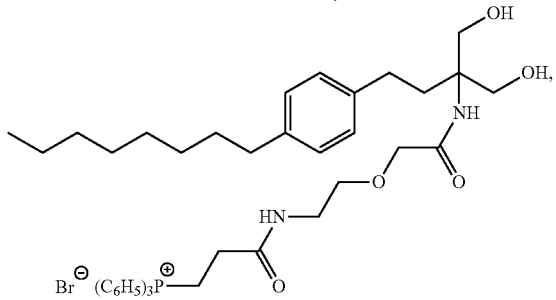

and

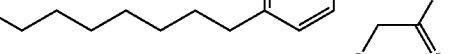

The FTY720 composition is in the form of a free form FTY720 or a pharmaceutically acceptable FTY720 salt. The FTY720 composition is administered orally. The FTY720 composition is co-administered with at least one active agent shown to have clinical activity against at least one motor symptom of Parkinson's Disease. The FTY720 composition is administered to the subject prior to the onset of at least one motor symptom of Parkinson's Disease.

The present disclosure provides an effective amount of 2-amino-2-[2-(4-octylphenyl)ethyl]propane-1,3-diol composition, (N-(1-hydroxy-2-(hydroxymethyl)-4-(4-octylphenyl)butan-2-yl)ethanamide), ((3-(1-hydroxy-2-(hydroxymethyl)-4-(4-octylphenyl)butan-2-ylamino)-3-oxopropyl) triphenylphosphonium bromide) for treating, alleviating or delaying progression of Parkinson's Disease in a subject in need thereof. The composition may include at least one additional active agent shown to have clinical activity against at least one symptom of demyelinating disease. The at least one active agent comprises an effective amount of an immunosuppressant, a corticosteroid, an immunoglobulin or a combination thereof.

The present disclosure provides a method of preventing at least one motor symptom of Parkinson's Disease in a subject suspected of having Parkinson's Disease by diagnosing a subject as having at least one symptom of Parkinson's Disease; and administering to the subject an effective amount of a FTY720 composition to prevent at least one motor symptom of Parkinson's Disease, wherein the FTY720 composition is selected from

FTY720-C2

FTY720-Mitoxy

-continued

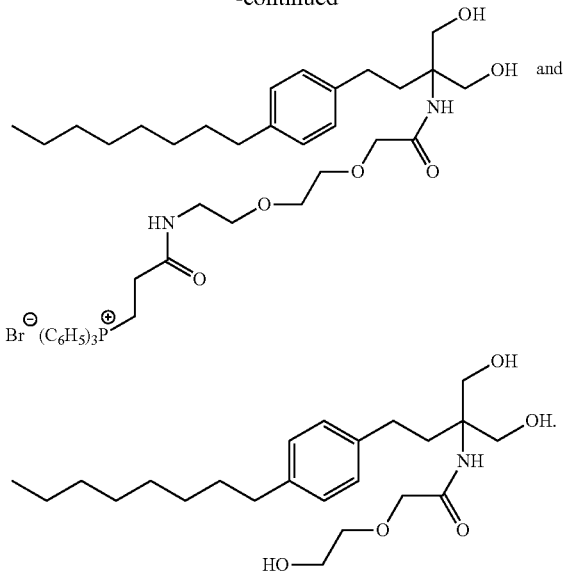

The FTY720 composition is in the form of a free form FTY720 or a pharmaceutically acceptable FTY720 salt. The FTY720 composition is administered orally. The FTY720 composition is co-administered with at least one active agent shown to have clinical activity against at least one motor symptom of Parkinson's Disease. The FTY720 composition is administered to the subject prior to the onset of at least one motor symptom of Parkinson's Disease.

The present disclosure provides a method of alleviating at least one symptom of Parkinson's Disease in a subject suspected of having Parkinson's Disease by diagnosing a subject as having at least one symptom of Parkinson's Disease; and administering to the subject an effective amount of a FTY720 composition to ameliorate at least one symptom of Parkinson's Disease. The FTY720 composition is 2-amino-2-[2-(4-octylphenyl)ethyl]propane-1,3-diol, 2-amino-2-[2-(4-octylphenyl)ethyl]propane-1,3-diol phosphate, (N-(1-hydroxy-2-(hydroxymethyl)-4-(4-octylphenyl)butan-2-yl)ethanamide), ((3-(1-hydroxy-2-(hydroxymethyl)-4-(4-octylphenyl)butan-2-ylamino)-3-oxopropyl)triphenylphosphonium bromide) or a derivative thereof. The FTY720 composition is in the form of a free form FTY720 or a pharmaceutically acceptable FTY720 salt. The FTY720 composition is administered orally. The FTY720 composition is co-administered with at least one active agent shown to have clinical activity against at least one symptom of Parkinson's Disease. The at least one active agent comprises an effective amount of an immunosuppressant, a corticosteroid, an immunoglobulin or a combination thereof. The FTY720 composition is administered to the subject after the onset of symptoms of Parkinson's Disease.

The present disclosure provides a method for treating, alleviating or delaying progression of Parkinson's Disease in a subject in need thereof by administering to the subject an effective amount of a 2-amino-2-[2-(4-octylphenyl)ethyl] propane-1,3-diol composition, (N-(1-hydroxy-2-(hydroxymethyl)-4-(4-octylphenyl)butan-2-yl)ethanamide), ((3-(1-hydroxy-2-(hydroxymethyl)-4-(4-octylphenyl)butan-2-ylamino)-3-oxopropyl)triphenylphosphonium bromide) or a derivative thereof to ameliorate at least one symptom of Parkinson's Disease. The method further comprising at least one additional active agent shown to have clinical activity against at least one symptom of demyelinating disease. The at least one active agent comprises an effective amount of an immunosuppressant, a corticosteroid, an immunoglobulin or a combination thereof.

The present disclosure provides a composition for treating, alleviating or delaying progression of the symptoms of Parkinson's Disease comprising: a pharmaceutical carrier containing a 2-amino-2-[2-(4-octylphenyl)ethyl]propane-1, 3-diol composition, a (N-(1-hydroxy-2-(hydroxymethyl)-4-(4-octylphenyl)butan-2-yl)ethanamide) composition, ((3-(1-hydroxy-2-(hydroxymethyl)-4-(4-octylphenyl)butan-2-ylamino)-3-oxopropyl)triphenylphosphonium bromide) composition or a derivative thereof in an effective amount to ameliorate at least one symptom of Parkinson's Disease. The 2-amino-2-[2-(4-octylphenyl) ethyl]propane-1,3-diol composition or a derivative thereof is in a free form or a pharmaceutically acceptable salt. The pharmaceutical carrier is formulated for oral delivery. The composition further comprising at least one additional active agent shown to have clinical activity against at least one symptom of a demyelinating disease. The at least one active agent comprises an effective amount of an immunosuppressant, a corticosteroid, an immunoglobulin or a combination thereof.

DESCRIPTION OF THE DRAWINGS

For a more complete understanding of the features and advantages of the present invention, reference is now made to the detailed description of the invention along with the accompanying figures and in which:

FIG. 1 shows the role of alpha-synuclein (Syn) on normal PP2A activity stimulation.

FIGS. 2A-F are images showing that Syn normally stimulates PP2A activity in mouse brain neurons. FIG. 2A is an image of immunoblots of striatal proteins. FIG. 2C shows immunohistochemistry. FIGS. 2B and 2D-2F are plots of enzyme activity assays and tyrosine hydroxylase phosphorylation.

FIG. 3A shows a Coomassie Stained gel of recombinant Syn that are soluble (Sol) or aggregated (Agg). FIG. 3B shows PP2A activity assays using recombinant soluble and aggregated Syn proteins. FIG. 3C shows Western blots of human brain frontal cortex showing equal amounts of PP2A. FIG. 3D shows impaired PP2A activity in human brain with Syn aggregation. FIGS. 3E and 3F show adrenal gland homogenates from aging Parkinson's Disease (PD) mouse model FIG. 3E shows a western blot Syn aggregation and FIG. 3F are plots showing that PD mice have equal PP2A levels but reduced PP2A activity in PD mouse adrenal gland with aggregated Syn. PD mice also exhibit anxiety.

FIG. 5 shows immunohistochemistry for tyrosine hydroxylase (TH) to label dopamine neurons (red column 1) Syn signal in the same cells (green column 2), in which paraquat (PQ) stimulates an increase in Syn. When PQ is given after FTY720, the compound blocks the increase in Syn, as can be appreciated in the merged image. FTY720 also reduces neuroinflammation as measured by microglial Ibal staining (green column 4) (on an adjacent tissue section, delineated by a red line between columns 3 and 4).

FIG. 6 shows that FTY720 stimulates BDNF trophic factor expression in neurons.

FIG. 7 shows that FTY720 improves mouse grip strength and reduces anxiety levels in control and mutant A53T Syn PD mice.

FIG. 8 shows that compounds, including some that can protect neurons against aggregated Syn, e.g. in the brains of individuals with Parkinson's disease, Dementia with Lewy Bodies, or Alzheimer's disease, can also stimulate PP2A activity.

FIG. 9A is a plot of serum levels of the parent FTY720-C2 molecule, after gavage measured by LC/MS. FIG. 9B is a plot of stimulatory effects of oral delivery of FTY720-C2 on PP2A in mouse adrenal gland for mice in 9A. FIG. 9C is a plot of serum levels of the parent, FTY720-C2 molecule, after IV delivery as measured by LC/MS. FIG. 9D is a plot of stimulatory effects of IV FTY720-C2 on PP2A in mouse adrenal gland for mice in 9C. FIG. 9E is a plot of serum levels of the parent, FTY720-Mitoxy molecule, after IV delivery as measured by LC/MS. FIG. 9F is a plot of stimulatory effects of IV FTY720-Mitoxy on PP2A in mouse adrenal gland for the mice evaluated in FIG. 9E.

DESCRIPTION OF EMBODIMENTS

Figure 1A:
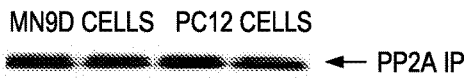
FIG. 1A is a blot showing equal PP2A amounts immunoprecipitated from cells.
Figure 1B:
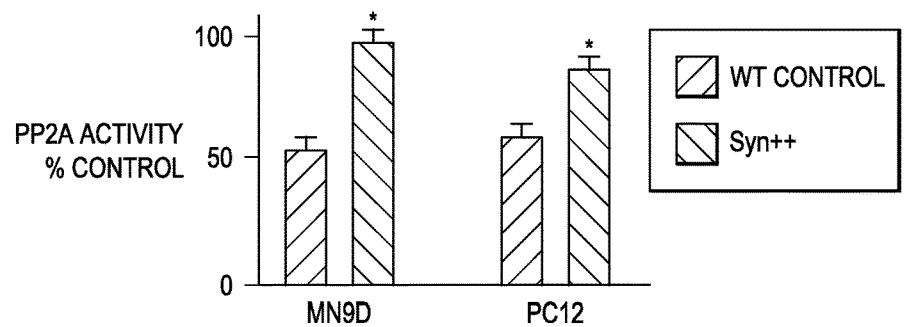
FIG. 1B and FIG. 1D are graphs demonstrating cellular PP2A activation by alpha-synuclein (Syn).
Figure 1C:
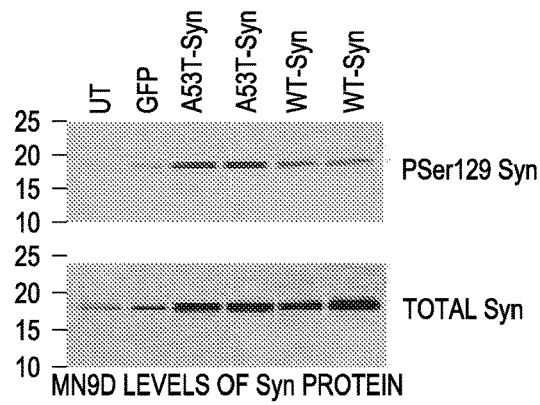
FIG. 1C is a blot showing protein levels of both phosphorylated and total Syn.
Figure 1D:
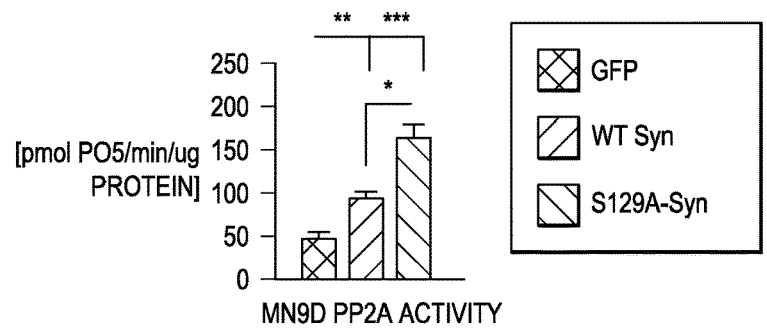

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the terms "Co-administration" or "Combined Administration" denotes administration of 2 or more therapeutic agents to a single patient, and include treatment regimens in which the agents are not necessarily administered by the same route of administration or at the same time.

As used herein the term "Injection," denotes all forms of injection known in the art such as subcutaneous, intraperitoneal, intramuscular, intraventricular (e.g., intracerebroventricular), intraparenchymal, intrathecal, and intracranial injection.

As used herein the term "Mammal" denotes any animal classified as a mammal, including humans, cows, horses, dogs, sheep, cats, rabbits, mice, and rats. In a preferred aspect, the mammal is a human.

As used herein the term "Parkinson's Disease" or "PD" denotes Parkinson's disease (shaking palsy); primary Parkinson's disease; secondary parkinsonism; postencephalitic parkinsonism; progressive supranuclear palsy; progressive pseudobulbar palsy; peroneal nerve palsy; Dystonia; Gaucher's disease; Gangliosidosis; Glucocerebrosidosis; Dementia with Lewy Bodies; Alzheimer's disease; Bell's palsy and generally as synucleinopathies.

As used herein the term "Oral" administration denotes the delivery of the formulation via the mouth through ingestion, or via any other part of the gastrointestinal system including the nose, mouth, esophagus or through suppository administration.

As used herein the phrase "Pharmaceutical Composition" denotes a composition useful for administration, e.g., in a Mammal, particularly a human subject. A pharmaceutical composition of the present invention is formulated to be compatible with its intended route of administration. Such formulations are well known in the art. Formulations that comprise therapeutically effective amounts of the FTY720 include, e.g., tablets, ampoules, capsules, sterile liquid solutions, liquid suspensions, or lyophilized versions, and optionally contain stabilizers or excipients, as described in detail herein. Lyophilized compositions are reconstituted with suitable diluents, e.g., water for injection, saline, 0.3% glycine and the like, at a level of about from 5 µg/kg of host body weight to approximately 0.07 mg/kg, 0.01 mg/kg to 1 mg/kg, 1 ng/kg to 1 mg/kg, or 1 µg/kg to 0.1 mg/kg/day, or more. The present invention also provides oral or parenteral compositions in dosage unit form for ease of administration and uniformity of dosage. Reagents, derivatives, and co-administered agents can be incorporated into pharmaceutical compositions suitable for administration. Such compositions can typically comprise FTY720 and a pharmaceutically acceptable carrier.

As used herein, "Pharmaceutically Acceptable Carrier," denotes any and all solvents, dispersion media, coatings, antibacterial and antifungal agents, isotonic and absorption delaying agents, and the like, compatible with pharmaceutical administration. The use of such media and agents for pharmaceutically active substances is well known in the art and include any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g., paraffin), absorbents (e.g., kaolin clay, bentonite clay), drug stabilizers (e.g., sodium lauryl sulphate), gels, binders (e.g., syrup, acacia, gelatin, sorbitol, tragacanth, polyvinylpyrrolidinone, carboxy-methyl-cellulose, alginates), excipients (e.g., lactose, milk sugar, polyethylene glycol), disintegration agents (e.g., agar-agar, starch, lactose, calcium phosphate, calcium carbonate, alginic acid, sorbitol, glycine), wetting agents (e.g., cetyl alcohol, glycerol monostearate), lubricants, absorption accelerators (e.g., quaternary ammonium salts), edible oils (e.g., almond oil, coconut oil, oily esters or propylene glycol), sweetening agents, flavoring agents, coloring agents, fillers (e.g., starch, lactose, sucrose, glucose, mannitol, silicic acid), tableting lubricants (e.g., magnesium stearate, starch, glucose, lactose, rice flower, chalk), carriers for inhalation (e.g., hydrocarbon propellants), buffering agents, or such like materials and combinations thereof, as would be known to one of ordinary skill in the art. Except insofar as any conventional carrier is incompatible with the active ingredient, its use in the therapeutic or pharmaceutical compositions is contemplated. In addition, pharmaceutically acceptable salts include the acid addition salts, e.g., those formed with the free amino groups of a proteinaceous composition or which are formed with inorganic acids such as, for example, hydrochloric, hydrobromic, or phosphoric acids; or such organic acids as acetic, oxalic, tartaric, benzoic, lactic, phosphoric, citric, maleic, fumaric, succinic, napsylic, clavulanic, stearic, or mandelic acid. Salts formed with the free carboxyl groups can also be derived from inorganic bases, e.g., sodium, potassium, ammonium, calcium magnesium or ferric hydroxides; or such organic bases as isopropylamine, trimethylamine, histidine or procaine.

As used herein the term "Parenteral" administration denotes the delivery of a composition, such as a composition comprising a neurogenesis modulating agent by a route other than through the gastrointestinal tract. In particular aspects, parenteral administration may be via intravenous, subcutaneous, intramuscular or intramedullary (i.e., intrathecal) injection or infusion.

As used herein the phrase "Therapeutically Effective Amount of an Agent" denotes the amount sufficient to improve one or more of the symptoms of the patient in need of treatment or at least to partially arrest the disease or its complications. Amounts effective for such use will depend on the severity of the disease and the general state of the patient's health. Multiple administrations may be required and the dosage and frequency will be dependent on the condition and the patient's tolerance.

As used herein the phrase "Topical" administration denotes the application of a pharmaceutical composition to the external surface of the skin or the mucous membranes (e.g., the surface membranes of the nose, lungs, and mouth) such that the agent crosses the external surface of the skin or mucous membrane and enters the underlying tissues. Application to the mucous membrane of the mouth may also be considered a form of oral administration. Topical administration of a pharmaceutical composition can result in a targeted distribution of FTY720 to the mucous membranes and surrounding tissues. The pharmaceutical composition may also be topically applied, so as to enter the bloodstream, and result in systemic distribution.

As used herein the term Fingolimod (FTY720) denotes the composition (2-amino-2-[2-(4-octylphenyl)ethyl]-1,3-propanediol). In addition the term also includes derivatives (e.g., phosphorylated FTY720 (e.g., FTY720-P) of the compositions known to the skilled artisan given the structure of FTY720 and its similarity to Sphingosine below respectively:

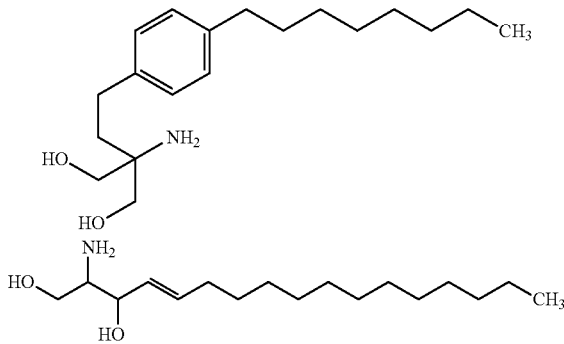

In general, FTY720 is an immunomodulatory agent that shares structural similarity with Sphingosine, which suggests that it acts via Sphingosine-1-phosphate (i.e., S1P) receptors. Fingolimod (FTY720) and the phosphorylated form (FTY720-P) are potent agonists of S1P receptors with the exception of S1P2.

The invention encompasses methods of alleviating one or more symptoms of a nervous system disorder by administering therapeutically effective amounts of FTY720 to a subject suffering from such disorder, with the proviso that the disorder is not multiple sclerosis (MS).

The invention also encompasses compositions and methods of preventing, reversing, and/or alleviating one or more symptoms of a nervous system disorder by administering therapeutically effective amounts of FTY720 related composition to a subject suffering from such disorder, e.g., the compositions may include:

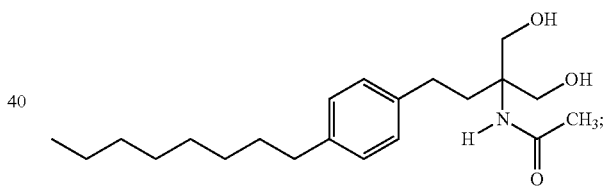

FTY720-C2

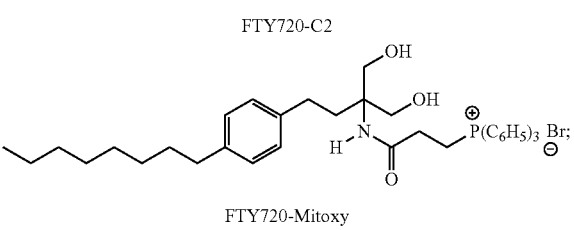

FTY720-Mitoxy

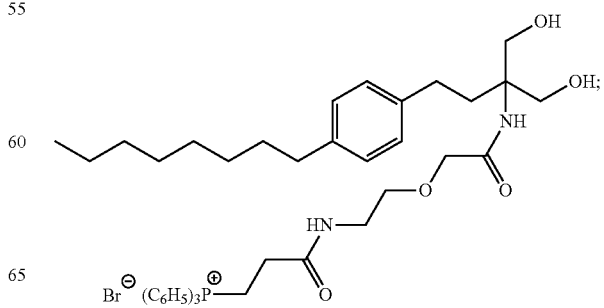

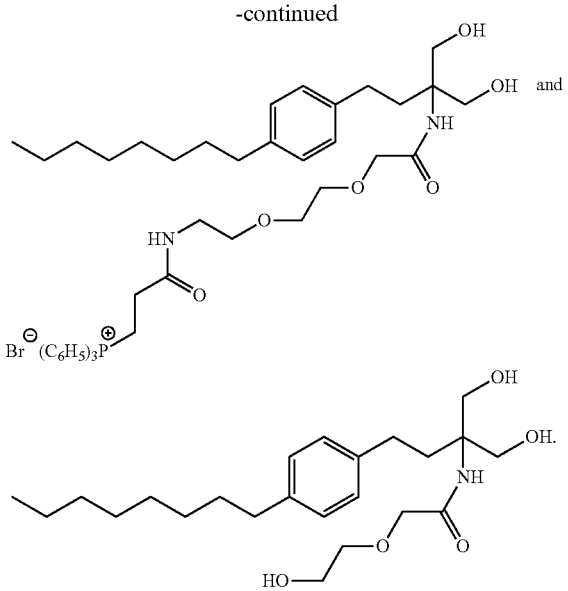

FTY720-C2 (N-(1-hydroxy-2-(hydroxymethyl)-4-(4-octylphenyl)butan-2-yl)ethanamide) is a synthetic carboxamide/C2-ceramide analogs of FTY720. FTY720-Mitoxy. ((3-(1-hydroxy-2-(hydroxymethyl)-4-(4-octylphenyl)butan-2-ylamino)-3-oxopropyl) triphenyl phosphonium bromide) incorporates a ceramide-like carboxamide with a cationic phosphonium group to provide intracellular delivery of the compound to the mitochondria. Also included are phosphorylated forms of FTY720-C2 and FTY720-Mitoxy.

For example, the present invention encompasses methods of alleviating one or more symptoms of Parkinson's disease or any form of synucleinopathy by administering therapeutically effective amounts of FTY720 to a subject suffering from such disorder. The present invention also encompasses methods of alleviating one or more symptoms of primary Parkinson's disease by administering therapeutically effective amounts of FTY720 to a subject suffering from such disorder. The present invention also encompasses methods of alleviating one or more symptoms of secondary parkinsonism and postencephalitic parkinsonism by administering therapeutically effective amounts of FTY720 to a subject suffering from such disorder.

The present invention encompasses methods of administering a composition comprising FTY720 to a subject suffering from Parkinson's disease to reduce alpha-synuclein levels; block alpha-synuclein aggregation; and restore normal PP2A activity to brain, thereby keeping proteins at an optimal phosphorylation state. In accordance with such methods, FTY720 is provided in a suitable formulation through a suitable route of administration, so as to reduce alpha-synuclein overexpression, sustain normal levels of alpha-synuclein in a soluble form, and sustain normal PP2A activity and normal protein phosphorylation.

In a particular aspect, the invention includes methods of administering an FTY720 composition to a mammal. The invention includes methods for treating one or more symptoms of Parkinson's disease in a subject by administering an FTY720 composition to the subject in order to modulate the activity of PP2A up or down based on the dose of the FTY720, FTY720-C2, and/or FTY720-Mitoxy used.

In accordance with the present invention, non-limiting examples include nervous system disorders, for example, at least the following: neurodegenerative disorders, In further aspects of the invention, the disorder of the nervous system includes, at least, dementia, epilepsy, injury related to epilepsy, and temporal lobe epilepsy. Also included are spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, spinal cord injury related to environmental toxin. In specific aspects of the invention, the disorder of the nervous system includes, at least, Parkinson's disease (shaking palsy), including primary Parkinson's disease, secondary parkinsonism, and postencephalitic parkinsonism; drug-induced movement disorders, including parkinsonism, acute dystonia, tardive dyskinesia, and neuroleptic malignant syndrome; Huntington's disease (Huntington's chorea; chronic progressive chorea; hereditary chorea); delirium (acute confusional state); dementia; Alzheimer's disease; non-Alzheimer's dementias, including Lewy body dementia, vascular dementia, Binswanger's dementia (subcortical arteriosclerotic encephalopathy), dementia pugilistica, normal-pressure hydrocephalus, general paresis, frontotemporal dementia, multi-infarct dementia, and AIDS dementia; age-associated memory impairment (AAMI); amnesias, such as retrograde, anterograde, global, modality specific, transient, stable, and progressive amnesias, and posttraumatic amnesias, and Korsakoffs disease. Other specific disorders include idiopathic orthostatic hypotension, Shy-Drager syndrome, progressive supranuclear palsy (Steele-Richardson-Olszewski syndrome); structural lesions of the cerebellum, such as those associated with infarcts, hemorrhages, or tumors; spinocerebellar degenerations such as those associated with Friedreich's ataxia, abetalipoproteinemia (e.g., Bassen-Kornzweig syndrome, vitamin E deficiency), Refsum's disease (phytanic acid storage disease), cerebellar ataxias, multiple systems atrophy (olivopontocerebellar atrophy), ataxia-telangiectasia, and mitochondrial multisystem disorders; acute disseminated encephalomyelitis (postinfectious encephalomyelitis); adrenoleukodystrophy and adrenomyeloneuropathy; Leber's hereditary optic atrophy; HTLV-associated myelopathy; motor neuron disorders such as amyotrophic lateral sclerosis, progressive bulbar palsy, progressive muscular atrophy, primary lateral sclerosis and progressive pseudobulbar palsy, and spinal muscular atrophies such as type I spinal muscular atrophy (Werdnig-Hoffmann disease), type II (intermediate) spinal muscular atrophy, type III spinal muscular atrophy (Wohlfart-Kugelberg-Welander disease), and type IV spinal muscular atrophy. Additional specific disorders include plexus disorders such as plexopathy and acute brachial neuritis (neuralgic amyotrophy); peripheral neuropathies such as mononeuropathies, multiple mononeuropathies, and polyneuropathies, including ulnar nerve palsy, carpal tunnel syndrome, peroneal nerve palsy, radial nerve palsy, Guillain-Barré syndrome, chronic relapsing polyneuropathy, hereditary motor and sensory neuropathy, e.g., types I and II (Charcot-Marie-Tooth disease, peroneal muscular atrophy), and type III (hypertrophic interstitial neuropathy, Dejerine-Sottas disease); disorders of neuromuscular transmission, such as myasthenia gravis; neuroophthalmologic disorders such as Horner's syndrome, internuclear ophthalmoplegia, gaze palsies, and Parinaud's syndrome; cranial nerve palsies, trigeminal neuralgia (Tic Douloureux); Bell's palsy; and glossopharyngeal neuralgia; radiation-induced injury of the nervous system; chemotherapy-induced neuropathy (e.g., encephalopathy); taxol neuropathy; vincristine neuropathy; diabetic neuropathy; autonomic neuropathies; polyneuropathie; and mononeuropathies; and ischemic syndromes such as transient ischemic attacks, subclavian steal syndrome, drop attacks, ischemic stroke, spinal ischemia, hemorrhagic stroke, and brain infarction.

Encompassed by the invention are pharmaceutical compositions that are useful for the treatment of nervous system disorders. For example, the compositions include an FTY720 compound, which can be administered alone or in combination with the systemic or local co-administration of one or more additional agents. Such agents include anti-inflammatory factors, vitamins (such as Vitamin E), preservatives, ventricle wall permeability increasing factors, glial lineage preventing agents, anti-apoptotic agents, anti-stress medications, neuroprotectants, and anti-pyrogenics. The pharmaceutical compositions preferentially treat nervous system diseases by keeping the levels of alpha-synuclein low, preventing Lewy body formation, and sustaining normal PP2A activity.

The present invention also provides a method for administering to the subject an effective amount of a pharmaceutical composition that includes FTY720 in a dosage range of 0.001 ng/kg/day to 10 mg/kg/day, a dosage range of 0.01 ng/kg/day to 5 mg/kg/day, a dosage range of 0.1 ng/kg/day to 1 mg/kg/day, a dosage range of 100 ng/kg/day to 1 mg/kg/day, a dosage range of 1 ng/kg/day to 1 mg/kg/day or 1 µg/kg/day to 0.1 mg/kg/day. This method also comprises administering to the subject an effective amount of a pharmaceutical composition that includes FTY720 in a combination with a ventricle wall permeability increasing factor. This method comprises administering to the subject an effective amount of a pharmaceutical composition that includes FTY720 in combination with a locally or systemically co-administered agent.

Examples of routes of administration include oral, subcutaneous, intraperitoneal, intramuscular, intraventricular (e.g., intracerebroventricular), intraparenchymal, intrathecal, intracranial, buccal, mucosal, nasal, and rectal routes. A parenteral preparation can be formulated for delivery via ampoules, disposable syringes or multiple dose vials made of glass or plastic. In addition, the pharmaceutical composition and neuroprotective agent of the invention may be delivered as an eye drop, eye ointment, or nose drop. In case that the composition of the invention is used in the form of an eye drop, or a nasal drop, the solvent employed includes a sterile distilled water or saline, in particular a distilled water for injection. The concentration of the active compound usually ranges from 0.01 to 2.0 w/v %, and may be increased or decreased depending on the aim of use. The eye drop, or a nasal drop may further contain various additives such as a buffer, an isotonic agent, a solubilizing agent, a preservative, a viscosity-increasing agent, a chelating agent, a pH adjustor, or an aromatic. For the eye drop and nasal drop, the preservative may include, for example, a quaternary ammonium salt such as benzalkonium chloride, benzethonium chloride or cetyl pyridinium chloride, a parahydroxybenzoic acid ester such as methyl parahydroxybenzoate, ethyl parahydroxybenzoate, propyl parahydroxybenzoate or butyl parahydroxybenzoate, benzyl alcohol, phenethyl alcohol, sorbic acid or a salt thereof, thimerosal, chlorobutanol, sodium dehydroacetate, methylparaben or propylparaben. The viscosity-increasing agent may include, for example, polyvinylpyrrolidone, hydroxyethylcellulose, hydroxypropylcellulose, methylcellulose, hydroxypropyl-methylcellulose, or carboxymethylcellulose or a salt thereof. The chelating agent may include disodium edetate or citric acid and the like. The pH adjustor may include hydrochloric acid, citric acid, phosphoric acid, acetic acid, tartaric acid, sodium hydroxide, potassium hydroxide, sodium carbonate or sodium bicarbonate and the like. The aromatic may include 1-menthol, borneol, camphor (e.g., DL-camphor), eucalyptus oil, luteolin, carnosic acid, rosmarinic acid and the like. The eye drop and nasal drop can typically be adjusted to about pH 4.0 to about pH 8.5.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi.

The carrier can be a solvent or dispersion medium containing, e.g., water, ethanol, organic solvents, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include one or more isotonic agents, for example, sugars, polyalcohols, such as manitol, sorbitol, and sodium chloride in the composition. Prolonged absorption of the injectable compositions can be brought about by including in the composition an agent which delays absorption.

Sterile injectable solutions can be prepared by incorporating FTY720 in the required amount in an appropriate solvent with one or a combination of ingredients as required, followed by filtered sterilization. Generally, dispersions are prepared by incorporating FTY720 into a sterile vehicle that contains a basic dispersion medium. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, FTY720 can be incorporated with excipients and used in the form of tablets, troches, or capsules. Oral compositions can also be prepared using a fluid carrier for use as a mouthwash, wherein FTY720 in the fluid carrier is applied orally and swished and expectorated or swallowed. Pharmaceutically compatible binding agents, and/or adjuvant materials can be included as part of the composition. The tablets, pills, capsules, troches and the like can contain one or more of the following ingredients, or compounds of a similar nature: a binder (e.g., microcrystalline cellulose, gum tragacanth or gelatin); an excipient (e.g., starch or lactose); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); or a flavoring agent (e.g., peppermint, methyl salicylate, or orange flavoring).

For administration by inhalation, the compositions of the invention can be delivered in an aerosolized and or topical form to the human respiratory system (e.g., nasal, oral, tracheal, bronchial, and alveolar sites) using inhalers or nebulizers (e.g., nasal delivery). For example, metered dose inhalers, dry powder inhalers, aqueous-based inhalers or nose drops can be used.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or nasal suppositories. For transdermal administration, the FTY720 compositions of the invention can be formulated into ointments, salves, gels, or creams, other means for external application as generally known in the art. The FTY720 compositions can also be prepared in the form of nasal drops or sprays, or suppositories.

In one embodiment, FTY720 is prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiments, the reagent is administered in a composition comprising at least 75, 80, 85, 90, 95, 96, 97, 98, 99, 99.5, 99.9% pure FTY720. FTY720 is formulated in a medium providing maximum stability and the least formulation-related side effects. In addition to FTY720, the composition of the invention may typically include one or more protein carrier, buffer, isotonic salt, and/or stabilizer.

The FTY720 compositions of the present invention can be administered in any conventional form for administration of a lipid. FTY720 can be administered in any manner known in the art in which it may either pass through the blood-brain barrier. Methods for enhancing passage through the blood-brain barrier include minimizing the size of the factor, providing hydrophobic factors which may pass through more easily, conjugating the protein reagent or other agent to a carrier molecule that has a substantial permeability coefficient across the blood brain barrier.

FIG. 1 shows the role of alpha-synuclein (Syn) on PP2A activity stimulation. FIG. 1A is a blot showing equal PP2A amounts immunoprecipitated from cells. FIG. 1B and FIG. 1D are graphs demonstrating cellular PP2A activation by alpha-synuclein (Syn). FIG. 1C is a blot showing protein levels of both phosphorylated and total Syn.

The FTY720 parent compound increases rPP2A activity more at lower concentrations than at higher concentrations. At 10 uM FTY720, the increase is not significantly greater than rPP2A alone. FTY720-C2 produced the biggest effect on rPP2A, while FTY720-Mitoxy produced a moderate effect, with a significant inhibitory effect noted at 10 uM. Legend-Baseline rPP2A activity bar is purple, +FTY720 bars are yellow, +FTY720-C2 bars are green, +FTY720-Mitoxy bars are magenta. *=P<0.05, =P<0.01, *=P<0.001, NSD=not significantly different.

Figure 2C:
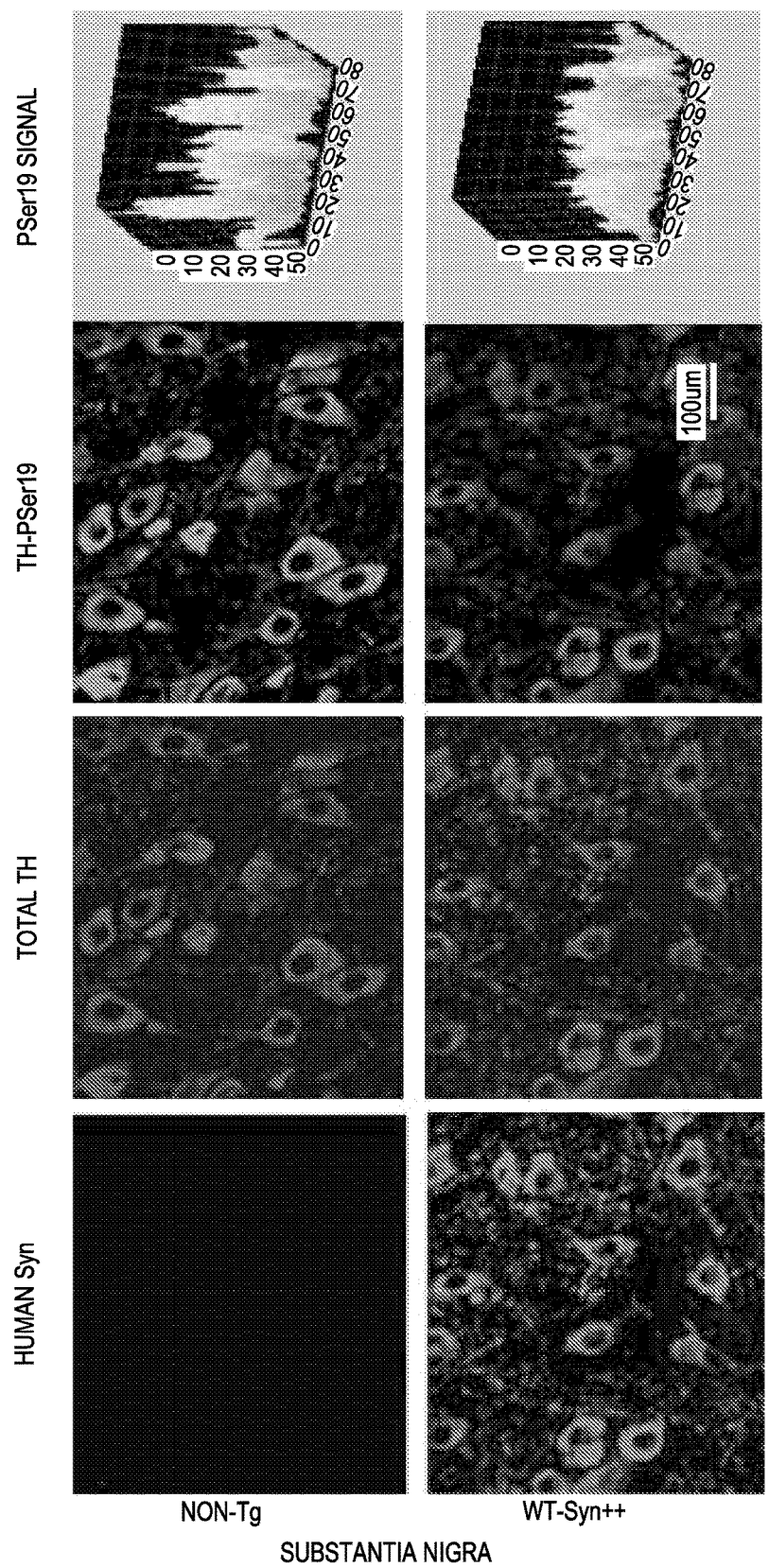

FIGS. 2A-F are images showing that Syn normally stimulates PP2A activity in mouse brain neurons. FIG. 2A is an image of immunoblots of striatal proteins. FIG. 2C shows immunohistochemistry. FIGS. 2B and 2D-2F are plots of enzyme activity assays and tyrosine hydroxylase phosphorylation.

Figure 3A:
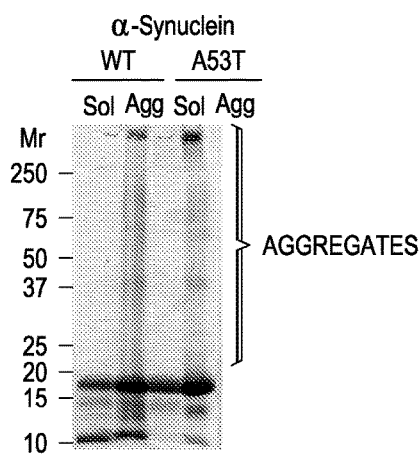
FIGS. 3A-3F show Syn aggregation reduces PP2A activity in Vitro and in Vivo.
Figure 3B:
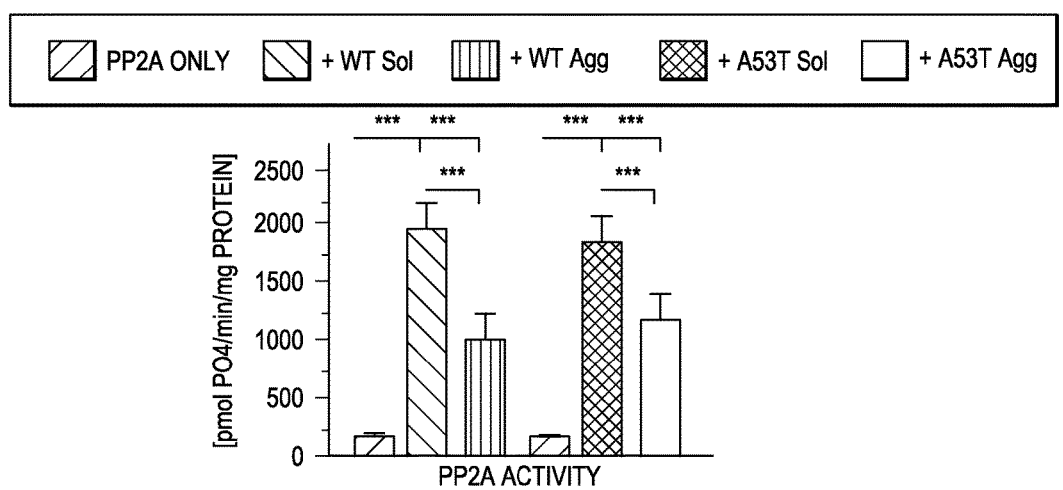
Figure 3C:
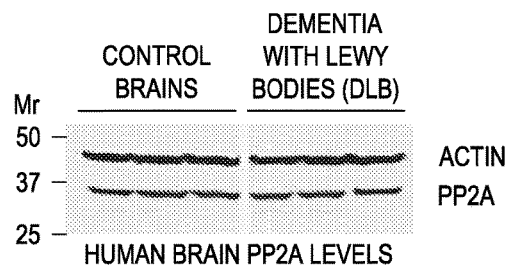
Figure 3D:
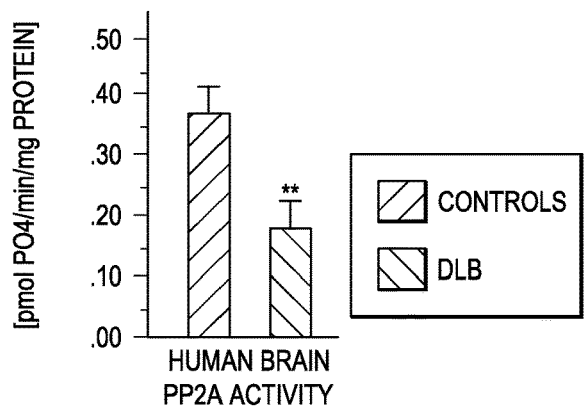
Figure 3E:
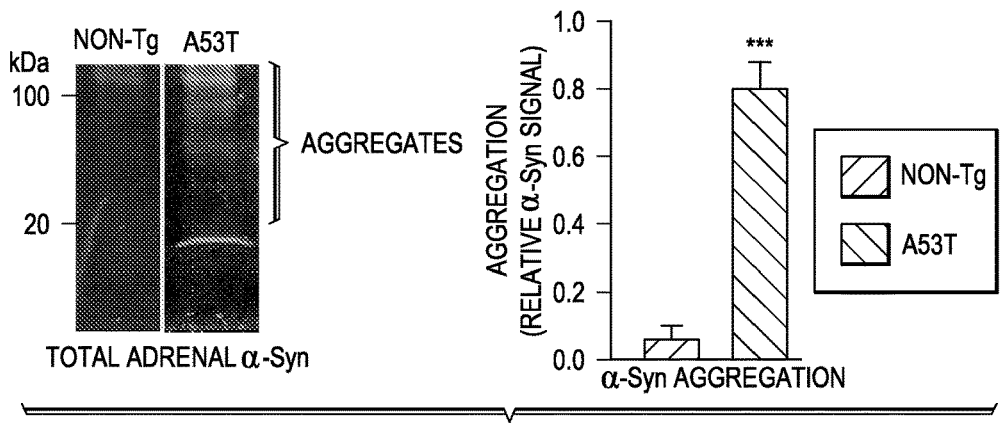
Figure 3F:
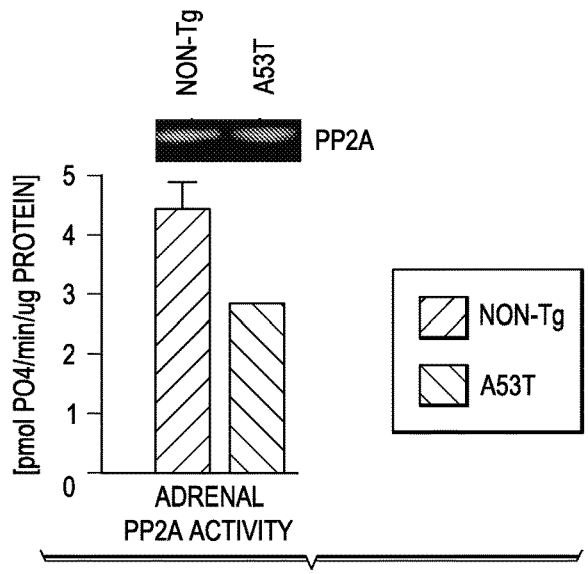

FIGS. 3A-3F show Syn aggregation reduces PP2A activity in Vitro and in Vivo. FIG. 3A shows a Coomassie Stained gel of recombinant Syn that are soluble (Sol) or aggregated (Agg). FIG. 3B shows PP2A activity assays using recombinant soluble and aggregated Syn proteins. FIG. 3C shows Western blots of human brain frontal cortex showing equal amounts of PP2A. FIG. 3D shows impaired PP2A activity in human brain with Syn aggregation. FIGS. 3E and 3F show adrenal gland homogenates from aging Parkinson's Disease (PD) mouse model FIG. 3E shows a western blot Syn aggregation and FIG. 3F are plots showing that PD mice have equal PP2A levels but reduced PP2A activity in PD mouse adrenal gland with aggregated Syn. PD mice also exhibit anxiety.

Figure 4A:
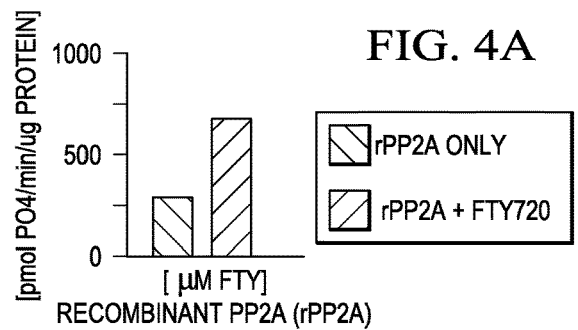
FIG. 4 shows that FTY720 stimulates PP2A activity in cell free (FIG. 4A) and cellular assays (FIG. 4B).
Figure 4B:
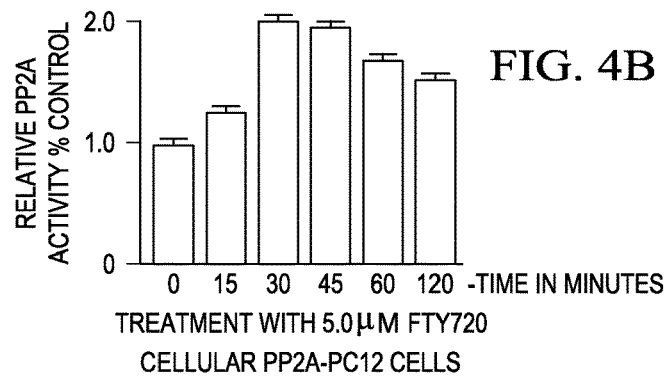

FIG. 4 shows that FTY720 stimulates PP2A activity in cell free (FIG. 4A) and cellular assays (FIG. 4B).

Figure 5:
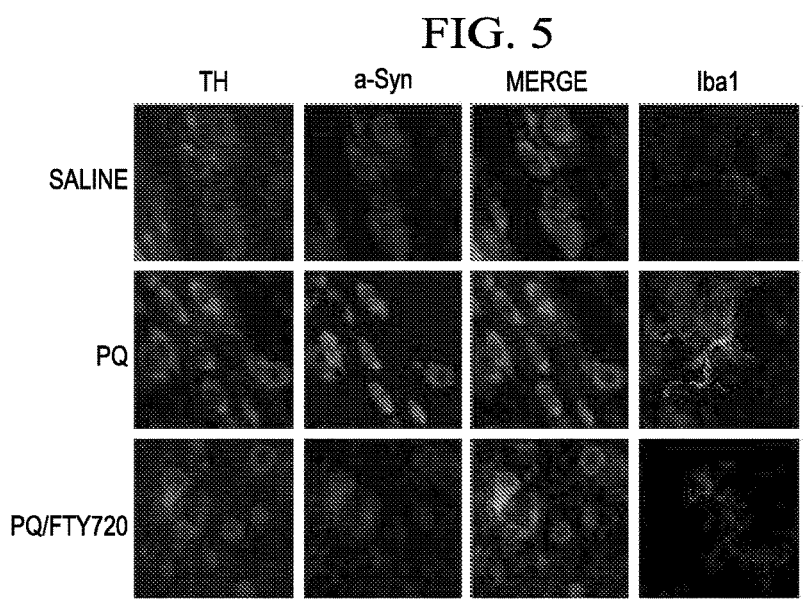
FIG. 5 contains images of brain tissues showing that FTY720 blocks Paraquat Toxicity in a C57/Bl6 Mice mouse model of Parkinson's disease.

FIG. 5 contains images of brain tissues showing that FTY720 blocks Paraquat Toxicity in a C57/B16 Mice mouse model of Parkinson's disease. FIG. 5 shows immunohistochemistry for tyrosine hydroxylase (TH) to label dopamine neurons (red column 1) Syn signal in the same cells (green column 2), in which paraquat (PQ) stimulates an increase in Syn. When PQ is given after FTY720, the compound blocks the increase in Syn, as can be appreciated in the merged image. FTY720 also reduces neuroinflammation as measured by microglial Ibal staining (green column 4) (on an adjacent tissue section, delineated by a red line between columns 3 and 4).

Figure 6A:
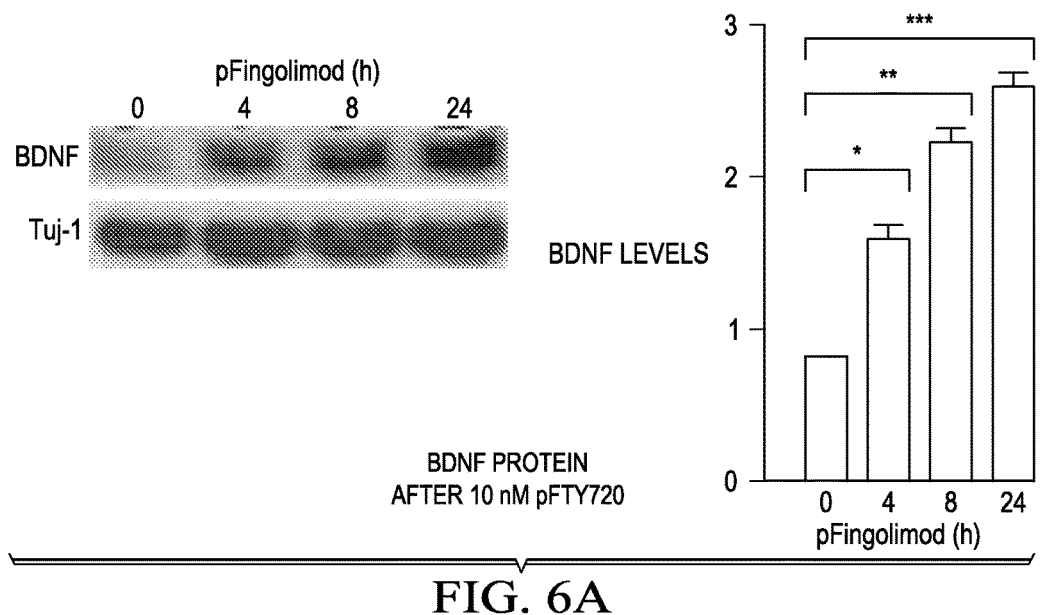
FIG. 6A shows a blot and a graph demonstrating that neurons treated with FTY720 have increased BDNF at the protein level and FIG. 6B is a plot showing increased BDNF expression at the message level.
Figure 6B:
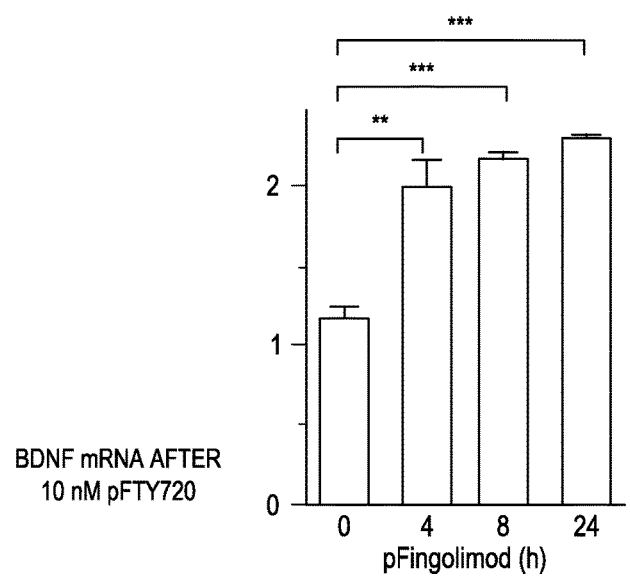

FIG. 6 shows that FTY720 stimulates BDNF trophic factor expression in neurons. FIG. 6A shows a blot and a graph demonstrating that neurons treated with FTY720 have increased BDNF at the protein level and FIG. 6B is a plot showing increased BDNF expression at the message level.

Figure 7A:
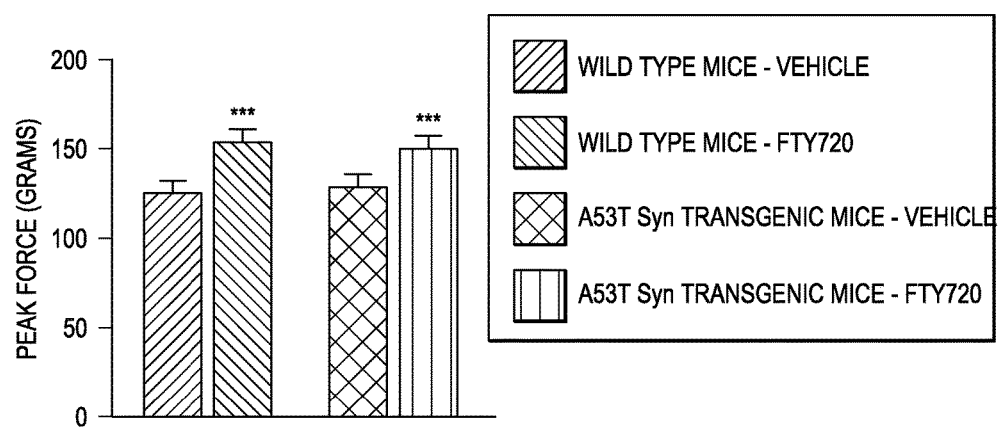
FIG. 7A shows that grip strength of 5 month old mice treated only with the delivery liquid (vehicle) was weaker than grip strength of mice treated with FTY720 twice a week for 14 weeks.
Figure 7B:
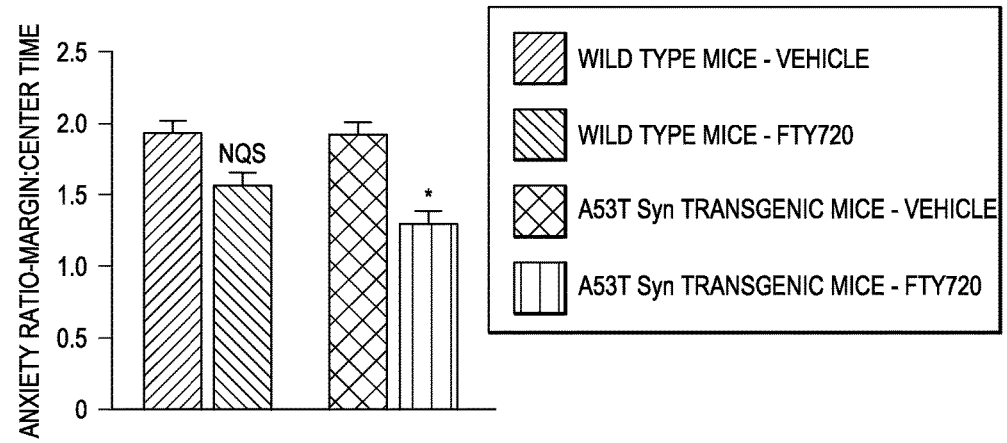
FIG. 7B shows that FTY720 reduces anxiety in mice (Vidal et al, in preparation).

FIG. 7 shows that FTY720 improves mouse grip strength and reduces anxiety levels in control and mutant A53T Syn PD mice. FIG. 7A shows that grip strength of 5 month old mice treated only with the delivery liquid (vehicle) was weaker than grip strength of mice treated with FTY720 twice a week for 14 weeks. FIG. 7B shows that FTY720 reduces anxiety in mice (Vidal et al, in preparation).

Figure 8A:
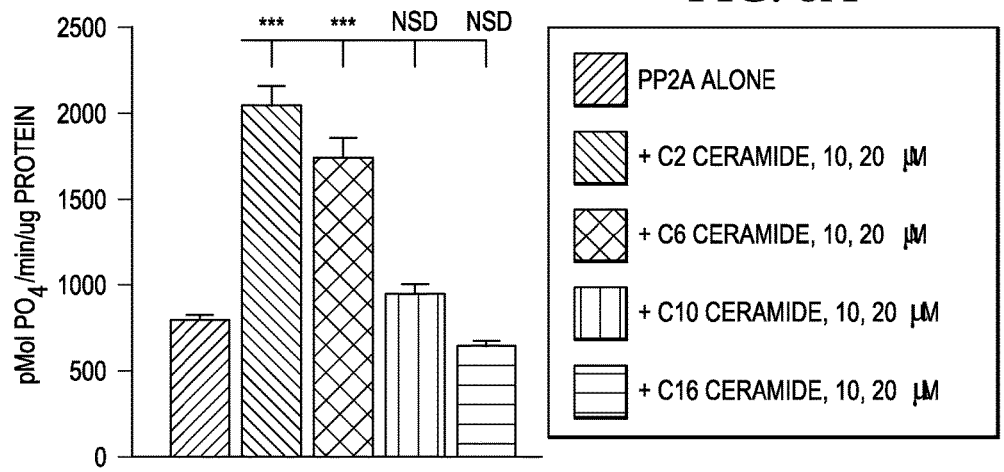
FIG. 8A is a plot that shows PP2A activity in response to Ceramides C2 and C6, which though able to stimulate PP2A activity, tend to be toxic, which is why they can be used to treat cancers.
Figure 8B:
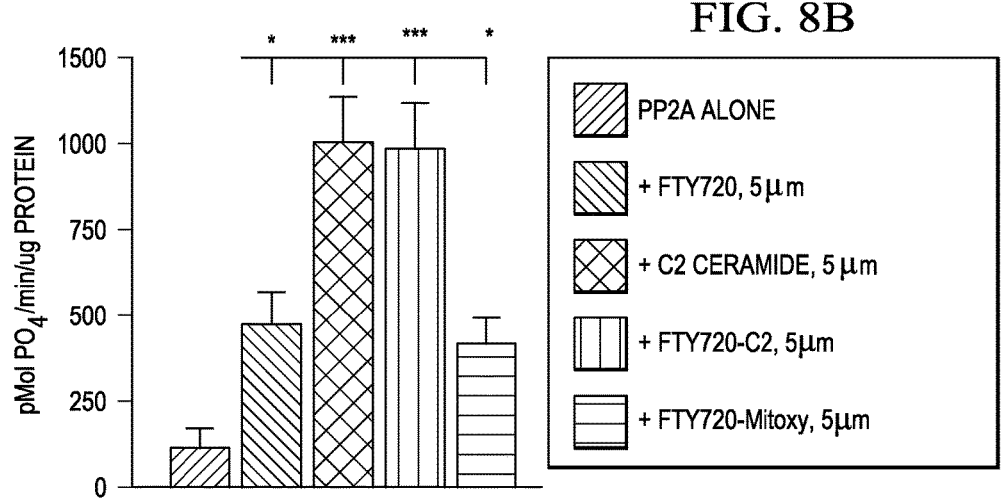
FIG. 8B is a plot that shows PP2A activity in response to neuroprotective anti-inflammatory FTY720, C2 ceramide (used as internal control), and potentially neuroprotective FTY720-C2 and FTY720-Mitoxy. All four compounds significantly stimulate PP2A activity.

FIG. 8 shows that compounds, including some that can protect neurons against aggregated Syn, e.g. in the brains of individuals with Parkinson's disease, Dementia with Lewy Bodies, or Alzheimer's disease, can also stimulate PP2A activity. FIG. 8A is a plot that shows PP2A activity in response to Ceramides C2 and C6, which though able to stimulate PP2A activity, tend to be toxic, which is why they can be used to treat cancers. FIG. 8B is a plot that shows PP2A activity in response to neuroprotective anti-inflammatory FTY720, C2 ceramide (used as internal control), and potentially neuroprotective FTY720-C2 and FTY720-Mitoxy. All four compounds significantly stimulate PP2A activity.

Figure 9A:
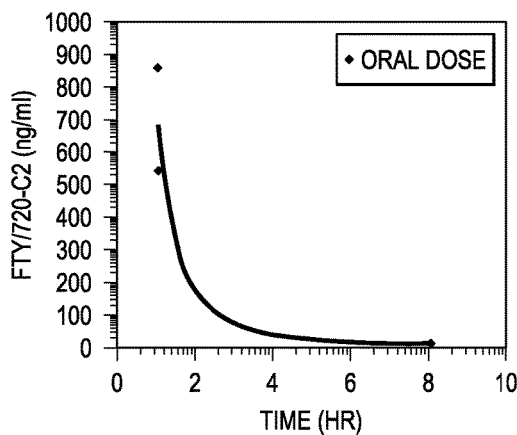
FIGS. 9A-9F show compositions of the instant disclosure tested for absorption and distribution by Ricerca Biosciences, LLC after single dosing of C57/Bl6 mice in which mice showed no ill effects in response to compounds. In-house testing of adrenal PP2A confirms in vivo activation.
Figure 9B:
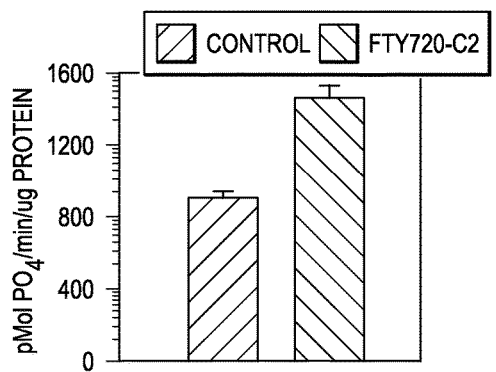
Figure 9C:
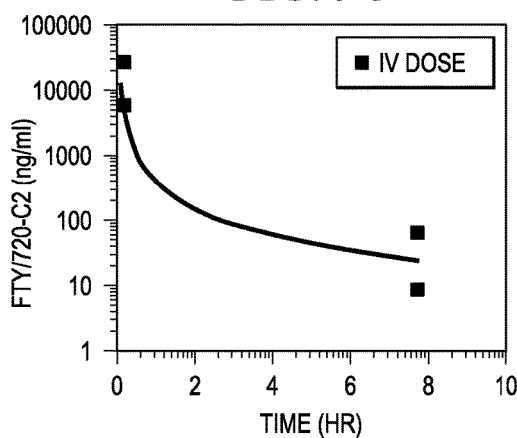
Figure 9D:
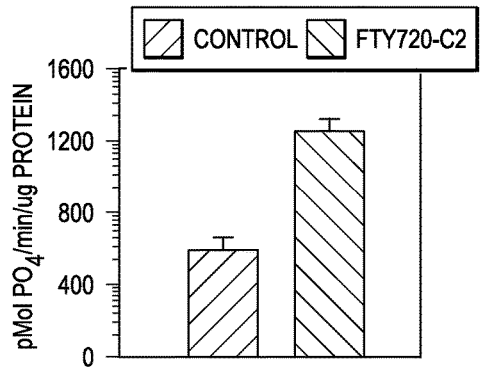
Figure 9E:
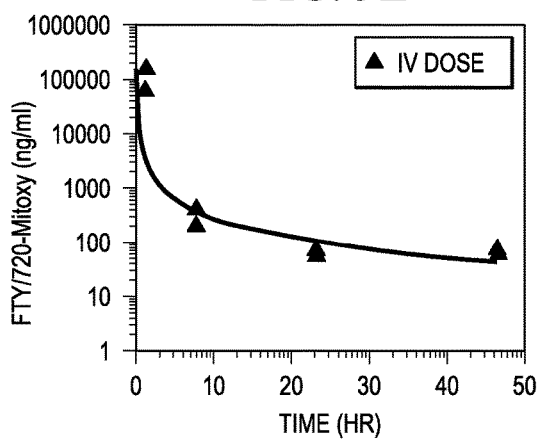
Figure 9F:
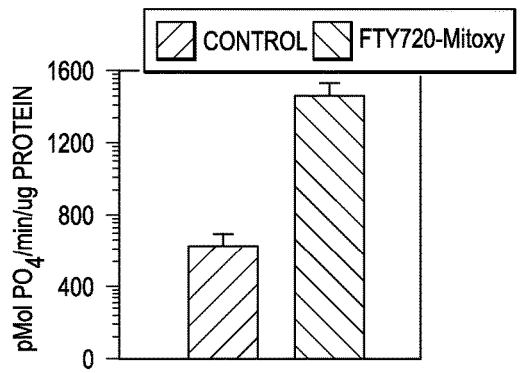

FIGS. 9A-9F show compositions of the instant disclosure tested for absorption and distribution by Ricerca Biosciences, LLC after single dosing of C57/B16 mice in which mice showed no ill effects in response to compounds. In-house testing of adrenal PP2A confirms in vivo activation. FIG. 9A is a plot of serum levels of the parent FTY720-C2 molecule, after gavage measured by LC/MS. FIG. 9B is a plot of stimulatory effects of oral delivery of FTY720-C2 on PP2A in mouse adrenal gland for mice in 9A. FIG. 9C is a plot of serum levels of the parent, FTY720-C2 molecule, after IV delivery as measured by LC/MS. FIG. 9D is a plot of stimulatory effects of IV FTY720-C2 on PP2A in mouse adrenal gland for mice in 9C. FIG. 9E is a plot of serum levels of the parent, FTY720-Mitoxy molecule, after IV delivery as measured by LC/MS. FIG. 9F is a plot of stimulatory effects of IV FTY720-Mitoxy on PP2A in mouse adrenal gland for the mice evaluated in FIG. 9E.

Supplementary active compounds can also be incorporated into the compositions. Modifications can be made to FTY720 to affect solubility or clearance of the molecule. Peptidic molecules may also be synthesized with D-amino acids to increase resistance to enzymatic degradation. In some cases, the composition can be co-administered with one or more solubilizing agents, preservatives, and permeation enhancing agents. Examples of pharmaceutically acceptable carriers include lactose, glucose, sucrose, sorbitol, mannitol, corn starch, crystalline cellulose, gum arabic, calcium phosphate, alginates, calcium silicate, microcrystalline cellulose, polyvinyl pyrrolidone, tragacanth gum, gelatin, serum, methyl cellulose, carboxymethyl cellulose, methylhydroxybenzoic acid esters, propylhydroxybenzoic acid esters, talc, magnesium stearates, inert polymers, water and mineral oils, e.g., the composition can include a preservative or a carrier such as proteins, carbohydrates, and compounds to increase the density of the pharmaceutical composition. The composition can also include isotonic salts and redox-control agents.

In some embodiments, the composition administered includes the reagent and one or more agents that increase the permeability of the ventricle wall, e.g., ventricle wall permeability enhancers. Such a composition can help an injected composition penetrate deeper than the ventricle wall. Examples of suitable ventricle wall permeability enhancers include, for example, liposomes, VEGF (vascular endothelial growth factor), IL, TNF-α, polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid and derivatives, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-β-cyclodextrin or other cyclodextrins.

In one aspect of the invention, a device can be implanted to administer the FTY720 composition to the ventricle. In another aspect, a cannula attached to an osmotic pump may be used to deliver the composition. Alternatively, the composition may be injected directly into the ventricles. The close proximity of the ventricles to many brain regions would allow for the diffusion of FTY720 into the brain.

For treatment of Parkinson's disease and other neurological disorders affecting primarily the midbrain and forebrain, FTY720 can be administered alone or with an additional agent or agents delivered to the ventricles of the forebrain. For example, Parkinson's disease is the result of low levels of dopamine in the brain, particularly the striatum. Normally the cell bodies of dopaminergic neurons are located in the substantia nigra and adjacent regions of the mesencephalon, with the axons projecting to the striatum. The methods and compositions of the invention provide an alternative to or a complement to the use of dopamine inducing drugs for treatment of Parkinson's disease.

Methods for preparing FTY720 dosage forms are known, or will be apparent, to those skilled in this art. The amount of FTY720 to be administered will depend upon the exact size and condition of the subject, but will be from, e.g., 1 ng to 1 mg, 1 μg to 0.1 mg, 1 mg to 100 mg, or preferably 0.3 mg to 10 mg in a volume of 0.001 ml to 10 ml. The duration of treatment and time period of administration of reagent will also vary according to the size and condition of the subject, the severity of the illness and the specific composition and method being used.

The actual dosage amount of a composition of the present invention administered to a patient can be determined by physical and physiological factors such as body weight, gender, severity of condition, the type of disease being treated, previous or concurrent therapeutic interventions, idiopathy of the patient, time of the administration, rate of excretion of the particular compound, and on the route of administration. The practitioner responsible for administration will, in any event, determine the concentration of active ingredient(s) in a composition and appropriate dose(s) for the individual subject.

In any case, the composition that further comprise various antioxidants to retard oxidation of one or more component. Examples of antioxidants includes ascorbic acid, cysteine hydrochloride, sodium sulfite, sodium bisulfate, sodium metabisulfite, ascorbyl palmitate, butylated hydroxytoluene, butylated hydroxyanisole, lecithin, propyl gallate, and tocopherol. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Aging, the main risk factor for Parkinson's disease (PD), stimulates increased α-synuclein levels in substantia nigra pars compacta (SNc). Excess α-synuclein spurs Lewy-like pathology and dysregulates the activity of protein phosphatase 2A (PP2A). PP2A dephosphorylates many neuroproteins, including the catecholamine rate-limiting enzyme, tyrosine hydroxylase (TH). A loss of nigral dopaminergic neurons induces PD movement problems, but before those abnormalities occur, behaviors such as olfactory loss, anxiety, and constipation often manifest. Identifying mouse models with early PD behavioral changes could provide a model in which to test emerging therapeutic compounds. To this end, we evaluated A53T α-synuclein mice for behavior and α-synuclein pathology in olfactory bulb, adrenal gland, and gut. Aging A53T mice exhibited olfactory loss and anxiety that paralleled olfactory and adrenal α-synuclein aggregation. PP2A activity was also diminished in olfactory and adrenal tissues harboring insoluble α-synuclein. Low adrenal PP2A activity co-occurred with TH hyperactivity, making this the first study to link adrenal synucleinopathy to anxiety and catecholamine dysregulation. Aggregated A53T α-synuclein recombinant protein had impaired stimulatory effects on soluble recombinant PP2A. Collectively, the data identify an excellent model in which to screen compounds for their ability to block the spread of α-synuclein pathology associated with premotor stages of PD. See Perez et al., (2013 Oct. 1). Non-Motor Parkinsonian Pathology in Aging A53T α-Synuclein Mice is Associated with Progressive Synucleinopathy and Altered Enzymatic Function. Journal of Neurochemistry, in press.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

What is claimed is:

1. A composition for treating, alleviating or delaying progression of the symptoms of Parkinson's Disease comprising:
   a pharmaceutical carrier containing
   an amount effective to ameliorate at least one symptom of Parkinson's Disease of one or more compositions having the formula

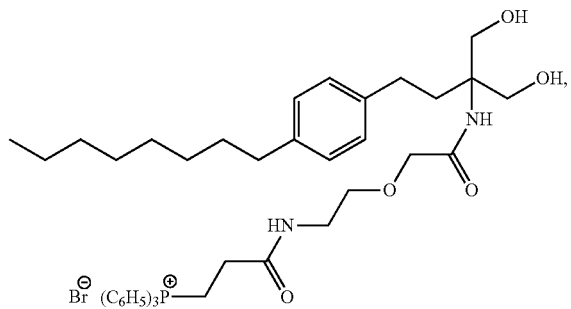

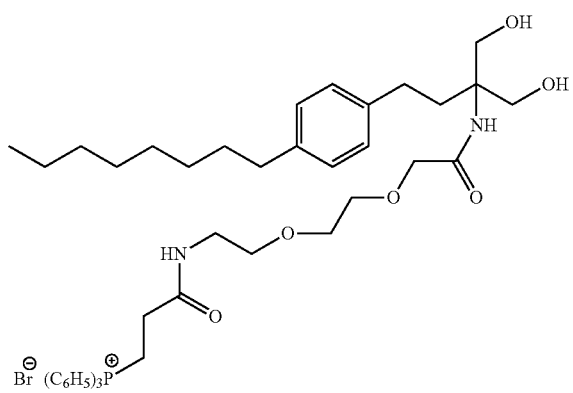

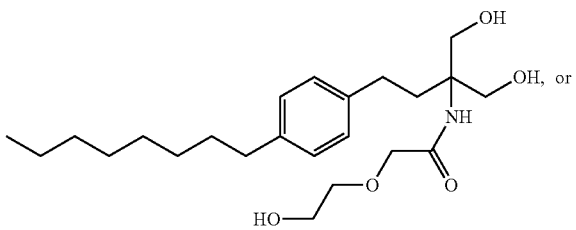

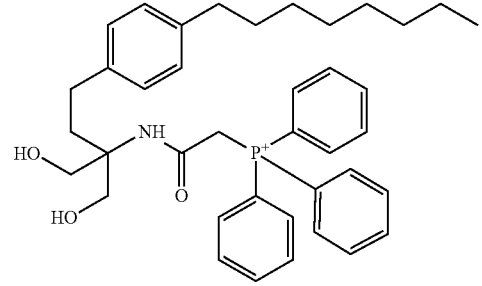

2. The composition of claim 1, wherein the pharmaceutical carrier is formulated for oral delivery.

3. The composition of claim 1, further comprising at least one additional active agent shown to have clinical activity against at least one symptom of a demyelinating disease.

4. The composition of claim 3, wherein the at least one active agent comprises an effective amount of an immunosuppressant, a corticosteroid, an immunoglobulin or a combination thereof.

5. The composition of claim 1, wherein the one or more compositions having the formula

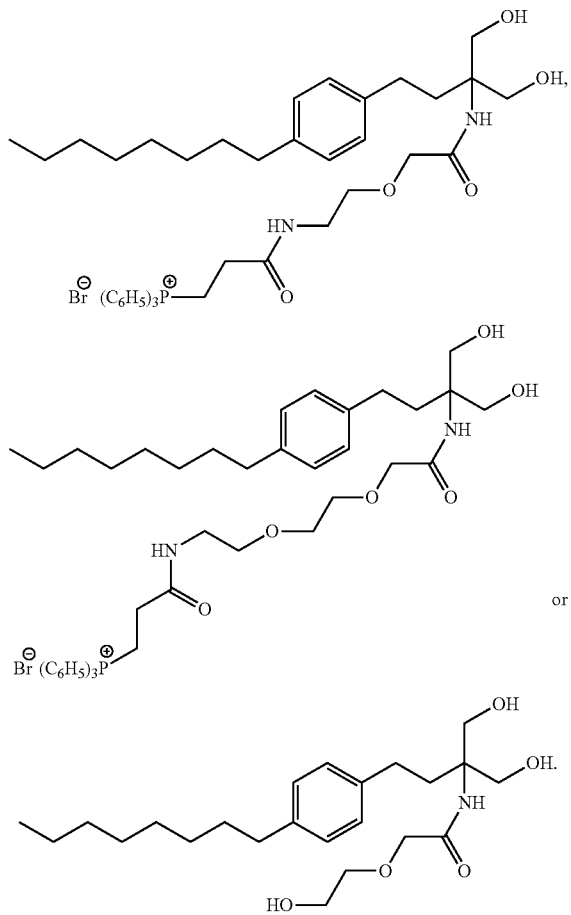

or

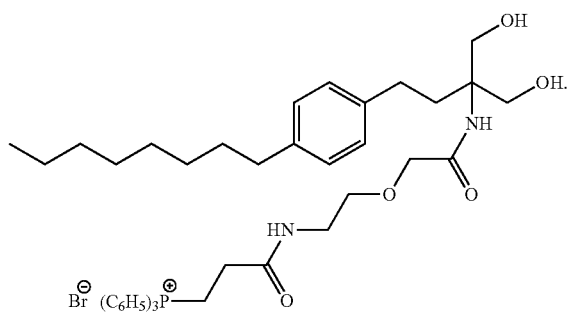

6. The composition of claim 1, wherein the one or more compositions having the formula 7. The composition of claim 1, wherein the one or more compositions having the formula

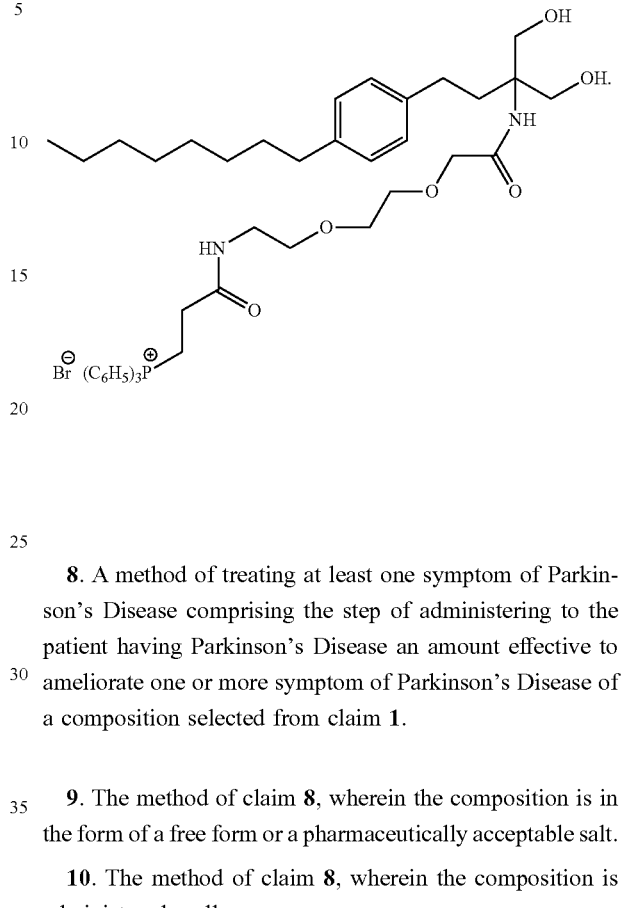

8. A method of treating at least one symptom of Parkinson's Disease comprising the step of administering to the patient having Parkinson's Disease an amount effective to ameliorate one or more symptom of Parkinson's Disease of a composition selected from claim 1.

9. The method of claim 8, wherein the composition is in the form of a free form or a pharmaceutically acceptable salt.

10. The method of claim 8, wherein the composition is administered orally.

11. The method of claim 8, wherein the composition is co-administered with at least one active agent shown to have clinical activity against at least one motor symptom of Parkinson's Disease.

12. The method of claim 8, wherein the composition is administered to the subject prior to the onset of at least one motor symptom of Parkinson's Disease.

13. The method of claim 8, further comprising an effective amount of at least one active agent selected from an immunosuppressant, a corticosteroid, and an immunoglobulin.

\* \* \* \* \*